(12) United States Patent
Cheng et al.

(10) Patent No.: US 9,772,407 B2
(45) Date of Patent: Sep. 26, 2017

(54) PHOTONIC-CHANNELED X-RAY DETECTOR ARRAY

(71) Applicant: The Board of Trustees of the Leland Stanford Junior University, Palo Alto, CA (US)

(72) Inventors: Yao-Te Cheng, New Taipei (TW); Lambertus Hesselink, Atherton, CA (US); Young-Sik Kim, Tuscon, AZ (US); Yuzuru Takashima, Cupertno, CA (US); Max Yuen, San Francisco, CA (US)

(73) Assignees: The Board of Trustees of the Leland Stanford Junior University, Palo Alto, CA (US); University of Arizona, Tucson, AZ (US)

( * ) Notice: Subject to any disclaimer, the term of this patent is extended or adjusted under 35 U.S.C. 154(b) by 0 days.

(21) Appl. No.: 15/230,199

(22) Filed: Aug. 5, 2016

(65) Prior Publication Data
US 2017/0038481 A1    Feb. 9, 2017

Related U.S. Application Data

(60) Provisional application No. 62/202,708, filed on Aug. 7, 2015.

(51) Int. Cl.
*G01T 1/20* (2006.01)
*G01T 1/202* (2006.01)
*G01N 23/04* (2006.01)

(52) U.S. Cl.
CPC .......... *G01T 1/2002* (2013.01); *G01N 23/04* (2013.01); *G01T 1/2018* (2013.01); *G01T 1/2023* (2013.01); *G21K 2207/005* (2013.01)

(58) Field of Classification Search
CPC ... G01T 1/2023; G01T 1/2018; G01T 1/2002; G01T 1/20; G01T 1/202; G21K 1/067; G01N 23/04
See application file for complete search history.

(56) References Cited

U.S. PATENT DOCUMENTS 6,180,946 B1 *  1/2001  Ebstein ............... G01T 1/20
                                              250/370.11

FOREIGN PATENT DOCUMENTS

DE   WO 2009118130 A1 * 10/2009 ......... G02B 21/0016

* cited by examiner

*Primary Examiner* — Marcus Taningco
*Assistant Examiner* — Faye Boosalis
(74) *Attorney, Agent, or Firm* — Lumen Patent Firm

(57) ABSTRACT

An X-ray detector array includes a scintillator that converts input X-ray radiation to secondary optical radiation output from the scintillator, a first telecentric micro lens array that array receives the secondary optical radiation, a phase coded aperture, where the first telecentric micro lens array directs the secondary optical radiation on the phase coded aperture, a second telecentric micro lens array, where the secondary optical radiation output from the phase coded array is directed to the second telecentric micro lens array, a patterned grating mask, where the second telecentric micro lens array directs the optical beam on the patterned mask, and a photodetector array, where the patterned mask outputs the optical beam in a pattern according to the patterned mask to the photodetector array, where the photodetector array outputs a signal, where a photon fringe pattern is imaged and sampled in the wavelength domain of the radiation from the scintillator.

9 Claims, 8 Drawing Sheets

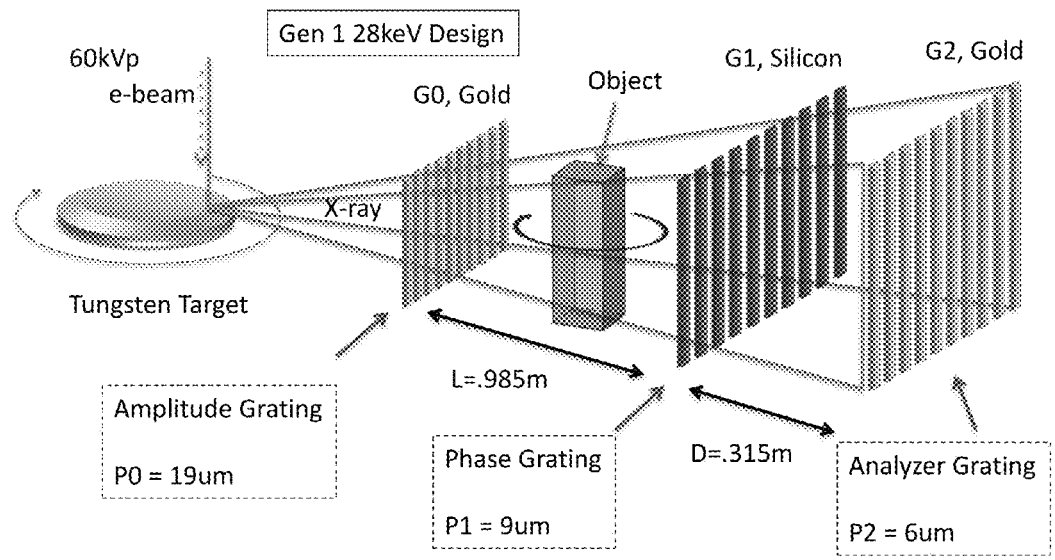
FIG. 1A  *Prior Art*
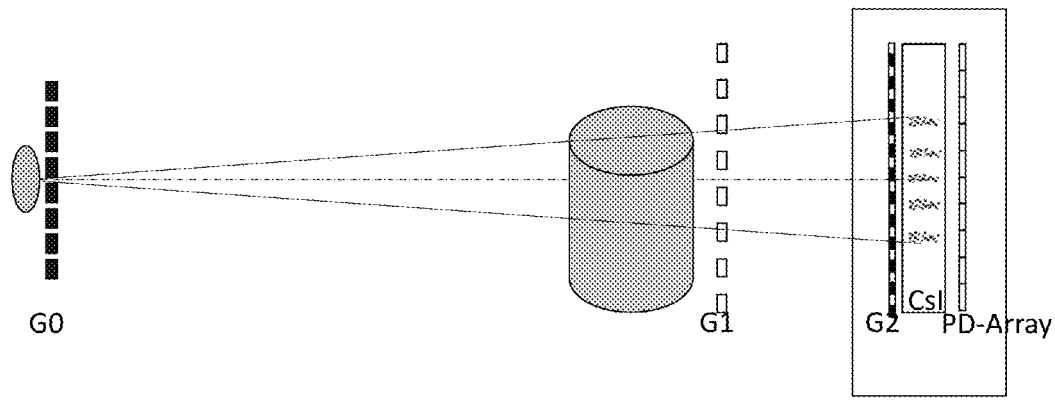
FIG. 1B  *Prior Art*

PHOTONIC-CHANNELED X-RAY DETECTOR ARRAY

CROSS-REFERENCE TO RELATED APPLICATIONS

This application claims priority from U.S. Provisional Patent Application 62/202,708 filed Aug. 7, 2015, which is incorporated herein by reference.

STATEMENT OF GOVERNMENT SPONSORED SUPPORT

This invention was made with Government support under contract HSHQDC-12-C-00002 awarded by the Department of Homeland Security. The Government has certain rights in the invention.

FIELD OF THE INVENTION

The invention relates to X-ray detection. More specifically, the invention relates an X-ray detector that eliminates an analyzer grating and enables motionless fringe detection having a large field of view.

BACKGROUND OF THE INVENTION

The index of refraction of an object in the visible wavelength domain range can be measured by interferometers, where the index of refraction in the X-ray domain can be measured by X-ray interferometry. In most of the interferometric measurement modalities, the fringe is formed by a coherent light source (for example laser) and optical components such as mirrors and lenses. Coherent light is split into two or more light beams, in either amplitude or space, by optical components such as a beam splitter and mirrors. One of the split beams (Object beam) passes through an object to be tested. The object induces an additional optical path length along the object beam. The modulation of the optical path is detected as a distortion of the fringe pattern by superposition of the other beam, (a reference beam) on top of the modulated object beam. The interferometric measurement is applicable for X-rays, however there are specific challenges for interferometric measurement in the X-ray domain. Coherent X-ray sources, such as synchrotron radiation light sources and X-ray lasers, are not as practical as coherent light sources in the visible domain. Also, the variation of X-ray optics is limited. For example, an X-ray lens has extremely small lens power due to the small differences in the index of refraction between air and the material. This lack of a handy coherent X-ray light source and the optical components for interferometry is overcome by Talbot interferometry by using an incoherent and a low brilliance X-ray source. FIG. 1 shows a schematic diagram of a prior art Talbot interferometry. In front of a conventional incoherent X-ray source such as electron-bombarded tungsten, an absorption grating (Silicon grating filled with Gold" Au/Si grating) is placed. Silicon is highly transparent to X-ray whereas Au is an absorptive material. The Si grating is filled with Au. The filled Au part blocks the X-rays, as a result, the Au/Si grating ($G_0$ grating) creates an array of line sources, which are partially coherent themselves but are mutually incoherent with each other. As each partially coherent line source emits a cylindrical wave, the cylindrical wave is diffracted by a second phase grating made of Silicon ($G_1$ grating). Generally, such a phase grating diffracts the incoming wave into multiple higher diffraction orders. As a special example, if the phase depth of the $G_0$ grating is tuned to Pi by adjusting the height of the grating wall to the specific X-ray wavelength, the phase profile is a rectangular one, only a plus and minus $1^{st}$ order diffraction wave exists. The diffracted cylindrical waves propagate and interfere with each other. As a result, a fractional Talbot fringe image is formed behind the $G_1$ grating. In the absence of an object, the fringe forms straight lines and the line lies along the $G_0$ and $G_1$ grating. With the presence of an object (either in front of or behind the $G_1$ grating), the straight fringe line is distorted due to the modulation of the phase along X-ray optical path. The distortion of the X-ray fringe is a spatial derivative of the phase profile induced by the object, and is detected by an X-ray detector array. The X-ray detector array includes a scintillator, which converts the X-ray photons to light photons, and a fiber optics plate, and photo diode array. To detect the X-ray fringe, another absorption grating ($G_2$ grating) is placed in front of the detector. Because the pitch of the fringe is generally much smaller than that of the photo detector array, the pitch of the $G_2$ grating is matched to that of the X-ray fringe. To detect the spatial distortion of the fringe line, the $G_2$ grating is mechanically scanned in a direction perpendicular to the fringe lines. At each scanning step, a signal is detected. Typically, the scanning step of the $G_2$ grating is ¼ or less of the pitch of the X-ray fringe. The detector signal is recorded as a function of the scanning step. Such a fringe scanning method, which is commonly used to detect phase from fringe pattern, is applied to detect the amount of the fringe distortion at each of the pixels. Finally, the induced phase by the object is computed by integrating the measured fringe distortion, using the relationship between the fringe shift and the spatial differential of the phase profile. Since the X-ray is not deflected severely by the object, the spatial phase distribution of the object is calculated by back tracing the x-ray from the detector to the source. This procedure reconstructs the spatial phase profile. A standard CT reconstruction algorithm can be also applied to reconstruct 3-D phase profile of the object.

The Talbot interferometer is an excellent way to enable X-ray interferometry without using a costly coherent X-ray source, by just using the three gratings. However there are fundamental drawbacks due to the usage of gratings: narrow field of view (FOV), a long data acquisition time due to mechanical motion of $G_2$ grating, and the costly and difficult fabrication of large gratings. This is especially true for applications for a wide FOV, and for high throughput application such as screening of a luggage at airport, where the small FOV and long scanning time is a serious problem.

Turning now to the scanning time, typically, the X-ray fringe is detected by mechanically scanning an analyzer grating ($G_2$ grating). The $G_2$ grating is a high aspect ratio grating made of Au, and is placed in front of a scintillator-based X-ray detector array. Such a mechanical scanning requires a high-precision control of motion of the grating (on the order of tens of nanometers), because at least four, ideally 16 steps of scanning is needed for typical X-ray fringe pitch of 5-10 µm. As a result the data acquisition rate is primarily limited by the mechanical scanning time.

Furthermore, the mechanical scanning becomes significantly more difficult, where the size of the grating increases as the size and weight of the Au/Si grating increases. For high X-ray photon energy applications, such as screening luggage at an airport, the fabrication of the Au/Si grating becomes a serious problem. Fabricating of the Au-grating having an area equivalent to the size of a piece of luggage (typically on the order of meter) is very difficult, where the fabrication process of the grating is basically a semiconductor process by using a Si substrate and employing lithography followed by anisotropic KOH etching, metallization, side wall passivation, and electroplating of Au. Fabrication of such a large grating is not easy because the need for a large area lithography machine, etching chamber and electroplating chamber, while controlling the process conditions for such a large area substrate. In addition to the size of the grating, the aspect ratio, meaning the ratio of the height of grating wall to the extent of opening region, becomes large (1 to 50 for 100 KeV X-ray photon energy), which imposes serious challenges for the grating fabrication. Ideally the wall height is on the order of couple of hundred micrometers (~500 um) for a high energy X-ray application, whereas the width of the opening is on the order of tens of micrometers. Thus the aspect ratio of the grating is 10 or larger. The fabrication of such a high aspect ratio grating having a square meter area is a serious challenge. In addition, the grating is technically a thin gold plate having an extent of a square meter and thickness of 250 µm, thus making the handling of such a Au plate a problem too.

For the FOV of a high aspect ratio grating is relatively very small (on the order of degrees), the high aspect ratio $G_2$ grating effectively detects the fringe if the X-ray propagates close to parallel to the grating side-wall, otherwise the $G_2$ grating does not provide sufficient contrast of the signal while stepping it. The FOV of the $G_2$ grating is approximated by ArcTan(1/AspectRatio)~1/AspectRatio. For an aspect ratio of 10, the FOV is only ±2.8 degrees, which is too small to inspect large object while limiting the overall length (eg. the source to detector distance) as small as 1-2 meters.

In summary, mechanical scanning of the Au/Si grating has several drawbacks, such as slow detection due to mechanical scanning, small FOV and costly and long lead time fabrication of high aspect ratio Au gratings.

What is needed is a detector system that eliminates the analyzer grating from the system, and enables for motionless fringe detection having a large FOV.

SUMMARY OF THE INVENTION

To address the needs in the art, an X-ray detector array is provided that includes a scintillator that converts input X-ray radiation to secondary optical radiation, where the secondary optical radiation is output from the scintillator, a first telecentric micro lens array that array receives the secondary optical radiation, a phase coded aperture, where the first telecentric micro lens array directs the secondary optical radiation on the phase coded aperture, a second telecentric micro lens array, where the secondary optical radiation output from the phase coded array is directed to the second telecentric micro lens array, a patterned grating mask, where the second telecentric micro lens array directs the optical beam on the patterned mask, and a photodetector array, where the patterned mask outputs the optical beam in a pattern according to the patterned mask to the photodetector array, where the photodetector array outputs a signal, where a photon fringe pattern is imaged and sampled in the wavelength domain of the radiation from the scintillator.

According to one aspect of the invention, the scintillator includes a CsI scintillator crystal.

In another aspect of the invention, the phase coded aperture includes a phase plate, where the phase plate has a cubic phase profile, where the phase plate is placed at a Fourier plane of the first telecentric micro lens array, where the phase plate is disposed to modify a point spread function, where the modified point spread function in an x-direction is constant over a depth of focus, where a point spread function in a y-direction increases with defocusing.

In yet another aspect of the invention, the patterned grating mask includes a chromium patterned grating mask. Here, the grating mask includes a photo processed absorption type mask.

According to a further aspect of the invention, the scintillator crystal has a thickness in a range of 0.001-1 mm.

In another aspect of the invention, each the telecentric micro lens array is arranged to form a 4-f imaging system.

According to one aspect of the invention, the patterned grating mask is placed at a focal plane of the second telecentric micro lens array.

In a further aspect of the invention, the X-ray detector array includes a depth of focus configured to detect a distortion of an X-ray fringe while capturing photons from an entire volume of the scintillator.

BRIEF DESCRIPTION OF THE DRAWINGS

FIGS. 1A-1B show a prior art conventional X-ray DPC imaging setup (1A) perspective view, (1B) top view.

DETAILED DESCRIPTION

Figure 2:
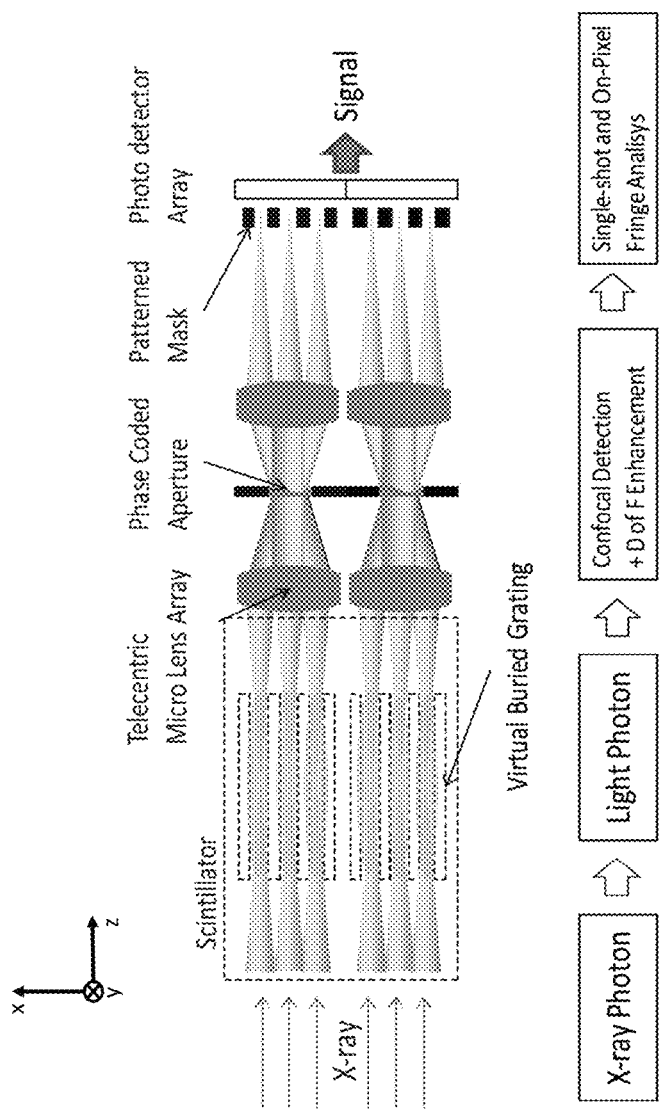
FIG. 2 shows a top view schematic diagram of the PcXDA, according to one embodiment of the invention.

To overcome such drawbacks of the detector in conventional Talbot X-ray fringe detection system, especially for high X-ray photon energy applications, the current invention provides a Photonic-channeled X-ray Detector Array (PcXDA) that eliminates the analyzer grating from the system, and enables for motionless fringe detection having a large FOV. FIG. 2 shows a schematic diagram of the PcXDA, according to one embodiment of the invention.

In a conventional X-ray detector, the X-ray fringe is sampled by the Au/Si $G_2$ grating, where the detection of the fringe distortion is carried out in the X-ray domain. The scintillator converts the sampled X-ray signal to visible photon. The photon is captured by and is transmitted through a fiber optics plate (FOP). Finally photo detector array integrates the photon signal over the region of the photo detector.

The PcXDA performs conversion of X-rays to visible photons by a scintillator. However, the detection of the fringe distortion is carried out in the visible photon domain. According to the embodiment shown in FIG. 2, the PcXDA includes 1) a scintillator, 2) micro lens array (MLA) based imaging optics, 3) a cubic phase plate, 4) a thin planer grating, and baffles to separate optical channel. Here, the X-ray fringe is converted to a photon fringe by a scintillator crystal. In one embodiment, the typical thickness of the scintillator crystal is 0.1-0.5 mm. The X-ray fringe pattern in the x-y plane, perpendicular to X-ray propagation direction, extends in z-direction, along the propagation direction of X-ray. As a result, X-ray fringe produces a 2.5 dimensional volumetric visible photon (x-y spatially varying profile extended along z-direction). The volumetric visible light pattern is imaged onto a photo diode/CMOS detector array by the MLA. The MLA is arranged to form a 4-f imaging system so that phase plate is inserted at the Fourier plane (back focal plane of the first MLA, as well as the front focal plane of the second MLA). In one embodiment, the pitch of the CMOS detector array is as small as on an order of a micrometer, therefore, the photon fringe having a pitch of tens of micrometers can be directly sampled by the photo detector array. Alternatively, for a large pitch photodetector array, a planer grating is placed at the back focal plane of the second MLA. The optical implementation enables detection of distortion of fringe in visible photon domain, as opposed to be carried out in X-ray domain for the conventional detector system. As a result, no high-aspect ratio Au/Si grating is needed because the photons can be blocked/absorbed by thin patterned grating mask made of for example Chromium (Cr). Yet, the MLA optics sharply sample the visible fringe in x-y plane at a specific location $z_0$ along z-axis, a contrast of photon fringe decreases because of the defocusing as $z_0$-z increases. Ideally, a sharp image of the volumetric fringe is needed, however due to the defocus effect, it is not needed in reality. For the PcXDA, a larger depth of focus (0.1-0.5 mm) is required to detect distortion of the fringe while capturing a larger amount of photons from the entire volume of the scintillator. To increase the depth of focus, a phase plate having a cubic phase profile, $A(x^3)$ where A is a coefficient, is placed at the Fourier plane of the first MLA (note that the phase plate can be inserted anywhere). The phase plate modifies a point spread function (PSF) such that the extent of the PSF in x-direction is constant over the depth of focus although the extent of the PSF in y-direction increases with defocusing. For X-ray DPC imaging, distortion of the fringe along x-direction is of interest, therefore the extent of the PSF in x-direction does matter. The cubic phase plate having x-profile thus performs extending depth of focus to detect distortion of the 2.5 dimensional volumetric fringe in high contrast, as well as being enable to collect visible photons from the entire volume of the scintillator.

Figure 3A:
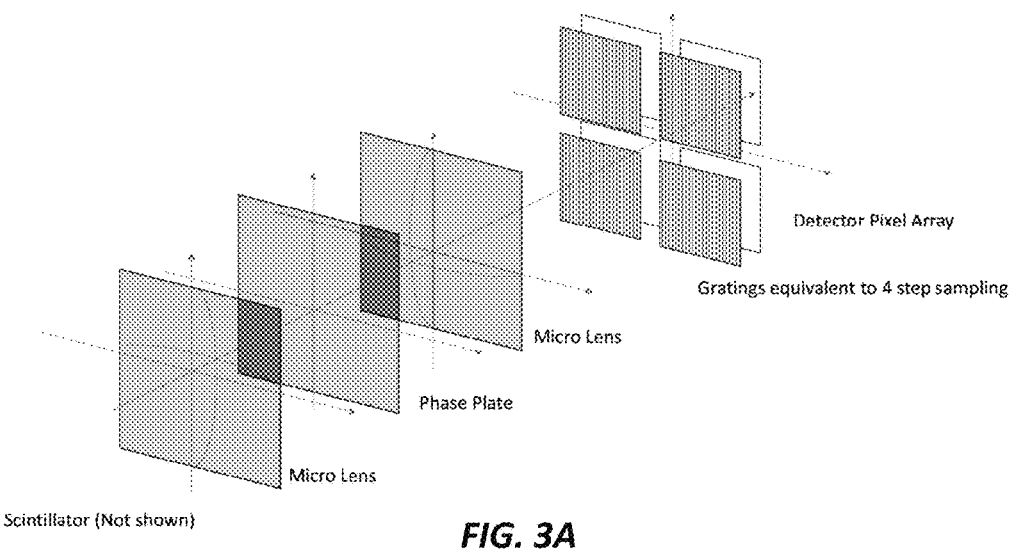
FIGS. 3A-3B show schematic diagrams of single shot DPC detection, (3A) perspective view of a channel of PcXDA for single shot phase detection, (3B) an example of arrangement of grating pattern among four pixels, according to the current invention.
Figure 3B:
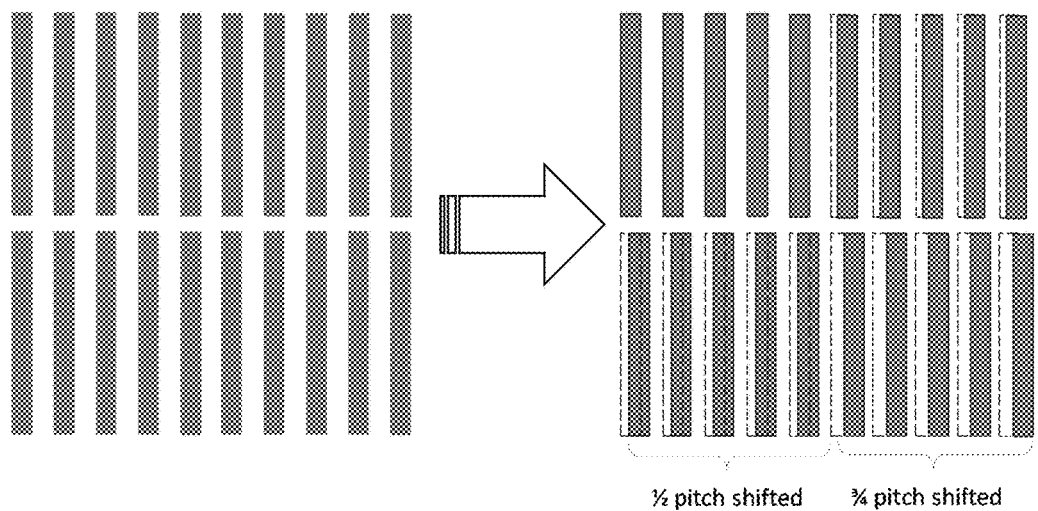

The optical implementation requires no high aspect ratio Au/Si grating. Therefore, the FOV can be drastically extended. In addition, a technique used for CMOS photo detector array can be applied to PcXDA to extend the FOV. For example, each of the micro lenses can be shifted with respect to the photodiode array to accommodate obliquely incident X-rays and a shifted and tilted visible fringe pattern, due to the obliquely incident X-ray. The PcXDA enables detection of the distortion of the fringe without mechanical scanning of a large and massive Au/Si grating. When a photo detector array with sufficiently (4 times or more) small pitch is compared to the X-ray fringe pitch, a shift of the X-ray fringe can be directly detected. For the larger detector pixel pitch compared to the X-ray fringe pitch, each PcXDA pixel has a shifted sampling grating with respect to each other (see FIGS. 3A-3B). For example, the PcXDA channel has a Cr mask at the image plane. In the adjacent optical channel, a Cr mask is placed at the image plane, though the mask pattern is shifted ¼ of the pitch of the X-ray fringe. By implementing two more Cr masks with shift of ½ and ¾ of the X-ray fringe pitch, each detector pixel works as a conventional and mechanically shifted $G_2$ grating while no step scanning of the $G_2$ grating is employed. Thus, a single-shot fringe detection, with no moving parts, is enabled by the optical implementation of the current invention.

Figure 4A:
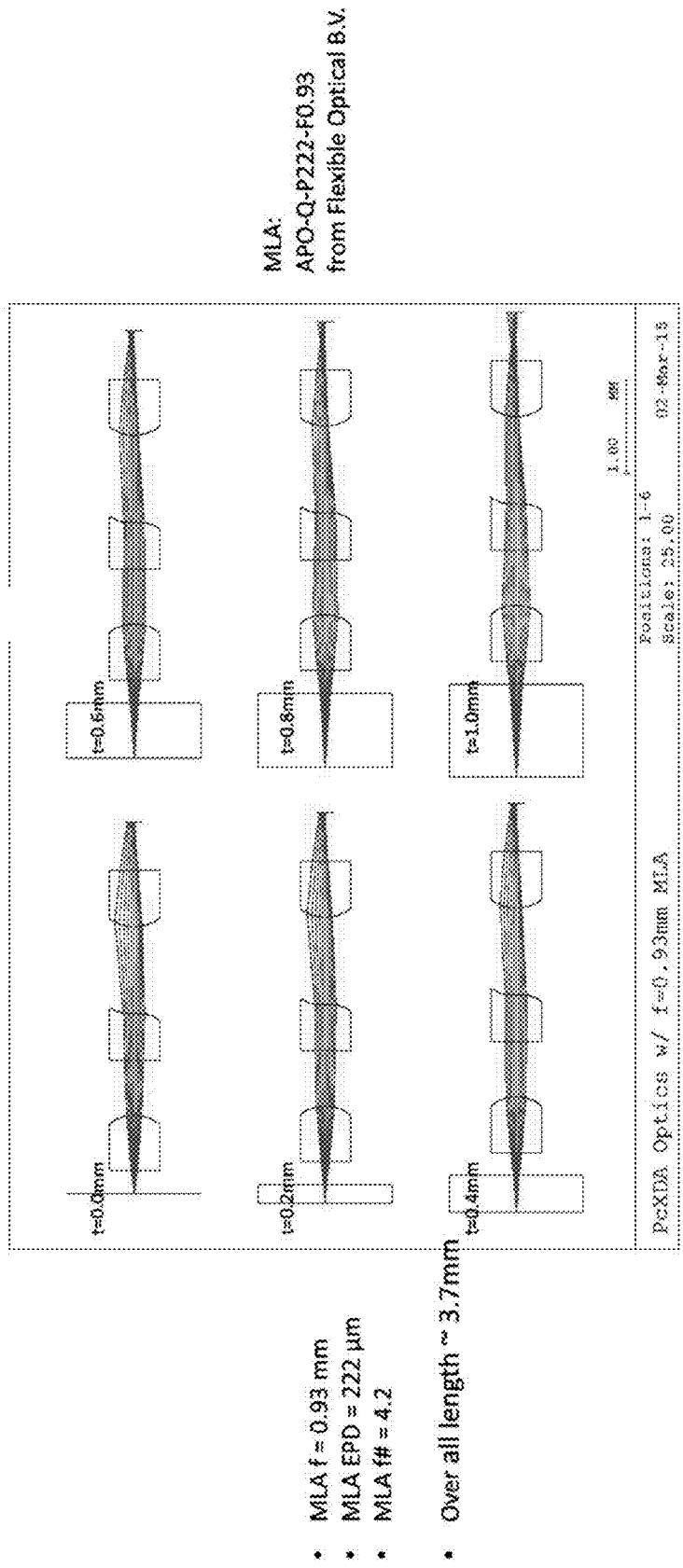
FIGS. 4A-4B show example top view designs of MLA optics for PcXDA, 4A) NA 0.12, and 4B) NA=0.22 for t=1 mm CsI scintillator according to the current invention.
Figure 4B:
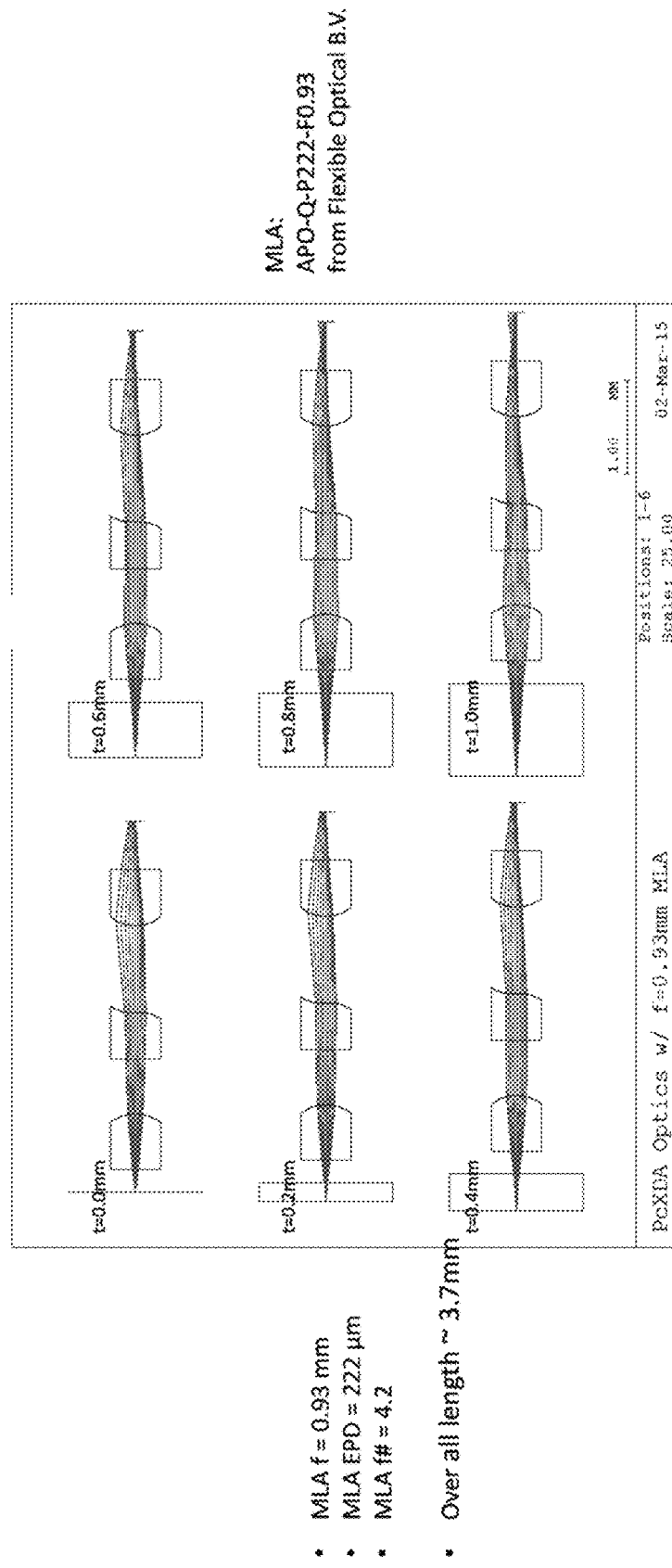

In FIGS. 4A-4B show example designs of MLA optics for PcXDA, according to exemplary embodiments of the current invention.

Figure 5:
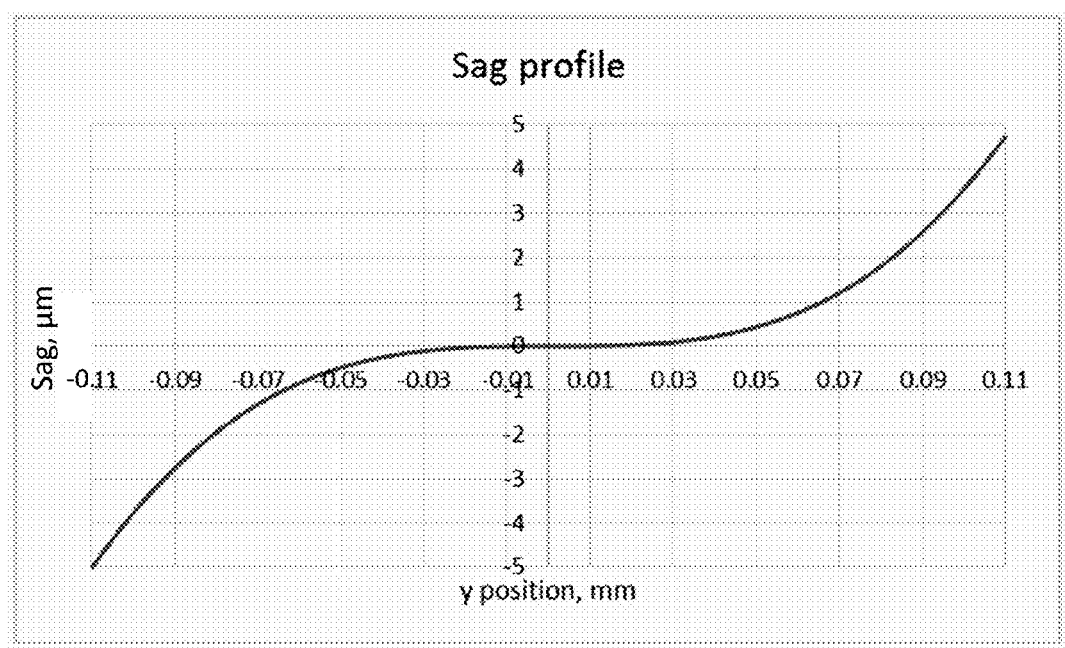
FIG. 5 shows the SAG profile of a phase plate, according to the current invention.

FIG. 5 shows the surface topology of a phase plate, according to the current invention.

The PcXDA solves fundamental problems, small FOV, long detection time of X-ray DPC imaging system employing mechanical scanning of a large and heavy and costly $G_2$ grating. Instead, a large FOV, and single shot fringe detection is feasible.

Figure 6A:
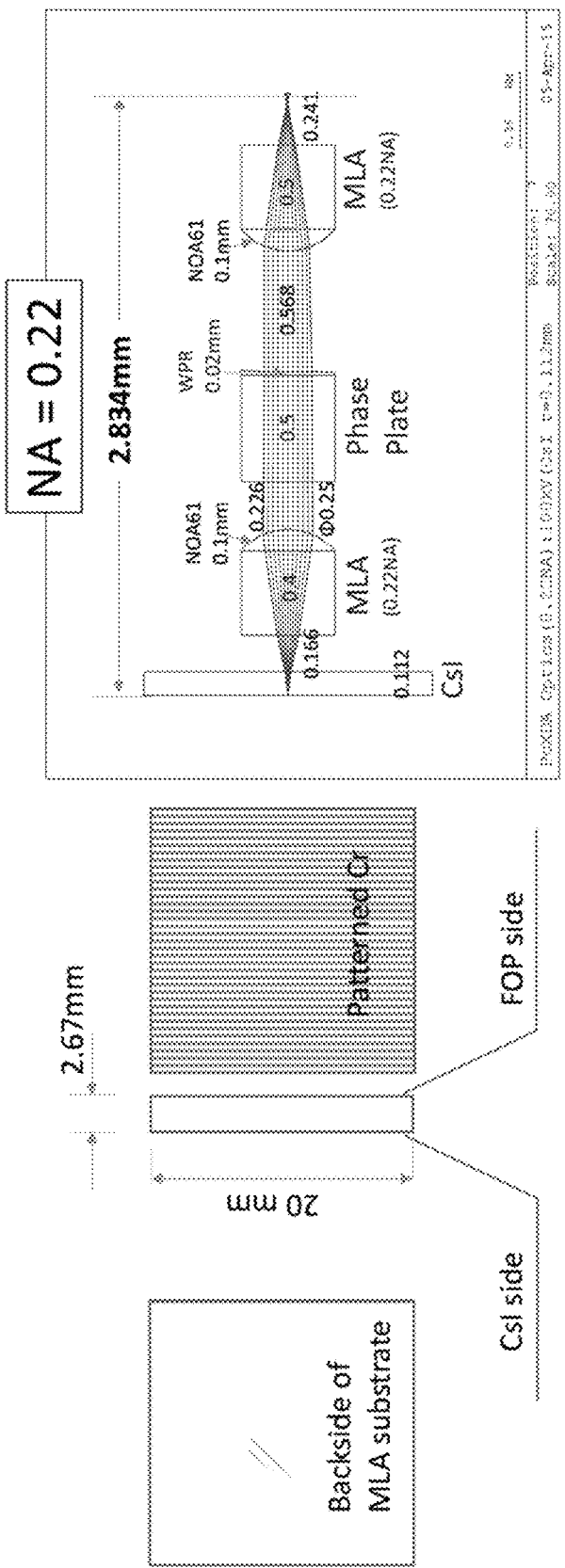
FIGS. 6A-6B show schematic views of an assembly of the PcXDA, according to embodiments of the current invention.
Figure 6B:
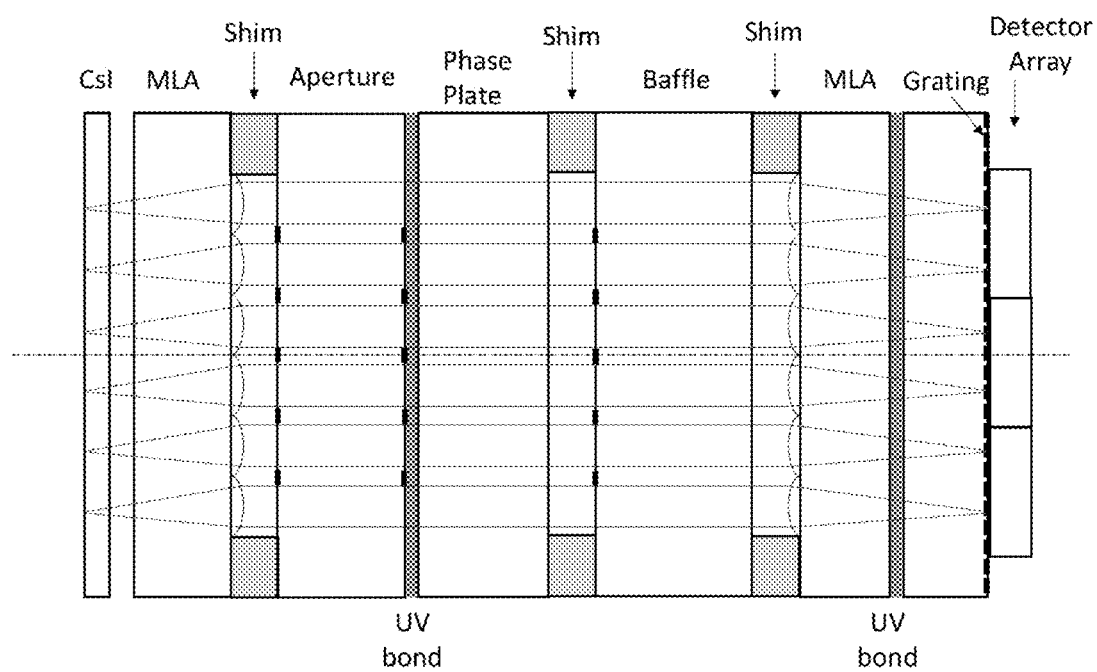

FIGS. 6A-6B show schematic views of an assembly of the PcXDA, according to embodiments of the current invention, where the invention overcomes all the drawbacks of the conventional grating based detection system.

The present invention has now been described in accordance with several exemplary to embodiments, which are intended to be illustrative in all aspects, rather than restrictive. Thus, the present invention is capable of many variations in detailed implementation, which may be derived from the description contained herein by a person of ordinary skill in the art. For example, static grating can be replaced with active device such as LCD and LCOS type of active shutter to actively scan optical fringes.

All such variations are considered to be within the scope and spirit of the present invention as defined by the following claims and their legal equivalents.

What is claimed:
1. An X-ray detector array, comprising:
   a) a scintillator, wherein said scintillator converts an input X-ray radiation to a secondary optical radiation, wherein said secondary optical radiation is output from said scintillator;
   b) a first telecentric micro lens array wherein said telecentric micro lens array receives said secondary optical radiation;
   c) a phase coded aperture, wherein said first telecentric micro lens array directs said secondary optical radiation on said phase coded aperture;
   d) a second telecentric micro lens array, wherein said secondary optical radiation output from said phase coded array is directed to said second telecentric micro lens array;
   e) a patterned grating mask, wherein said second telecentric micro lens array directs said optical beam on said patterned mask; and
   f) a photodetector array, wherein said patterned mask outputs said optical beam in a pattern according to said patterned mask to said photodetector array, wherein said photodetector array outputs a signal, wherein a photon fringe pattern is imaged and sampled in the wavelength domain of said radiation from said scintillator.

2. The X-ray detector array according to claim 1, wherein said scintillator comprises a CsI scintillator crystal.

3. The X-ray detector array according to claim 1, wherein said phase coded aperture comprises a phase plate, wherein said phase plate comprises a cubic phase profile, wherein said phase plate is placed at a Fourier plane of said first telecentric micro lens array, wherein said phase plate is disposed to modify a point spread function, wherein said modified point spread function in an x-direction is constant over a depth of focus, wherein a point spread function in a y-direction increases with defocusing.

4. The X-ray detector array according to claim 1, wherein said patterned grating mask comprises a chromium patterned grating mask.

5. The X-ray detector array according to claim 4, wherein said grating mask comprises a photo processed absorption time mask.

6. The X-ray detector array according to claim 1, wherein said scintillator crystal has a thickness in a range of 0.001-1 mm.

7. The X-ray detector array according to claim 1, wherein each said telecentric micro lens array is arranged to form a 4-f imaging system.

8. The X-ray detector array according to claim 1, wherein said patterned grating mask is placed at a focal plane of said second telecentric micro lens array.

9. The X-ray detector array according to claim 1, wherein said X-ray detector array comprises a depth of focus configured to detect a distortion of an X-ray fringe while capturing photons from an entire volume of said scintillator.

* * * * *